United States Patent [19]

Hocquaux et al.

[11] Patent Number: 4,973,474
[45] Date of Patent: Nov. 27, 1990

[54] 2,4-DIAMINOPYRIMIDINE 3-OXIDE DERIVATIVES AND THEIR USE FOR THE TREATMENT AND PREVENTION OF HAIR LOSS

[75] Inventors: Michel Hocquaux, Paris; Jacqueline Dumats, Villepinte; Quintino Gaetani, Sevran, all of France

[73] Assignee: L'Oreal, Paris, France

[21] Appl. No.: 387,590

[22] Filed: Jul. 31, 1989

[30] Foreign Application Priority Data

Aug. 1, 1988 [LU] Luxembourg .................. 87308

[51] Int. Cl.$^5$ .................. A61K 7/06; C07D 239/48
[52] U.S. Cl. .................. 424/70; 514/272; 544/320
[58] Field of Search .................. 514/272; 424/70; 544/320

[56] References Cited

FOREIGN PATENT DOCUMENTS

WO86/00616 7/1986 PCT Int'l Appl. .

Primary Examiner—Merrell C. Cashion, Jr.
Assistant Examiner—Susan S. Rucker
Attorney, Agent, or Firm—Fleit, Jacobson, Cohn, Price, Holman & Stern

[57] ABSTRACT

New 2,4-diaminopyrimidine 3-oxide derivatives and their use for the treatment and the prevention of hair loss.

The compounds correspond to the formula:

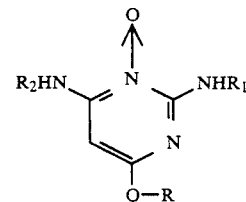

in which:

$R_1$ and $R_2$ denote hydrogen or the groups of formula:

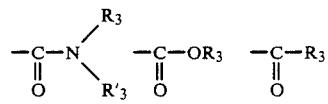

with $R'_3 = H$ or $R_3$, in which $R_3$ denotes alkyl, alkenyl or cycloalkyl; $R_3$ may also denote an aryl or aralkyl radical.

R denotes alkyl, alkenyl or cycloalkyl capable of bearing an unsaturation or alkyl bearing an aromatic or heterocyclic nucleus.

18 Claims, No Drawings

2,4-DIAMINOPYRIMIDINE 3-OXIDE DERIVATIVES AND THEIR USE FOR THE TREATMENT AND PREVENTION OF HAIR LOSS

The present invention relates to new pyrimidine 3-oxide derivatives, to their preparation and to cosmetic or pharmaceutical compositions intended especially to be employed by topical application in the treatment and prevention of hair loss.

6-Piperidino-2,4-diaminopyrimidine 3-oxide, or minoxidil, is already known in the state of the art for its properties as an antihypertensive agent, but also for its use in the treatment of hair loss, of pelada, of desquamative dermatitis, of alopecia and the like.

The applicants have just found new products derived from pyrimidine 3-oxide, substituted in position 6.

They found that these products were particularly effective for fresh hair growth, in particular for inducing and stimulating the growth of hair and delaying its loss, and could be employed, in particular, in the treatment of diseases of the scalp such as pelada, desquamative dermatitis and alopecia.

Furthermore, these compounds exhibit an antihypertensive activity which is appreciably weaker than that of minoxidil.

The subject of the invention is therefore new pyrimidine 3-oxide derivatives substituted in position 6.

Another subject of the invention consists of the process for their preparation.

The invention also relates to cosmetic and/or pharmaceutical compositions making use of these compounds.

Other subjects of the invention will become apparent on reading the description and the examples which follow.

The compounds in accordance with the invention are characterized essentially in that they correspond to the formula:

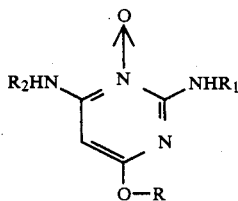

in which: $R_1$ and $R_2$ denote, independently of each other, a hydrogen atom, a carbamoyl group of formula:

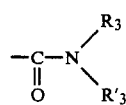

with $R'_3 = H$ or $R_3$; and alkoxycarbonyl group of formula:

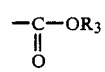

or an acyl group of formula:

in which formulae $R_3$ denotes a linear or branched $C_1-C_{18}$ alkyl radical, a $C_2-C_{18}$ alkenyl group or a $C_5-C_8$ cycloalkyl group; $R_3$ may also denote an aryl or aralkyl radical corresponding to the formula:

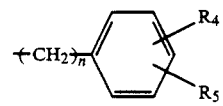

in which:

n is an integer which can vary between 0 and 4l;

$R_4$ and/or $R_5$, independently of each other, denote hydrogen, a lower $C_1-C_6$ alkyl group, a hydroxyl or $C_1-C_6$ alkoxy group, a halogen atom or a $CF_3$ group;

R denotes a linear or branched $C_1-C_{18}$ alkyl or $C_2-C_{18}$ alkenyl radical, a $C_4-C_6$ cycloalkyl radical capable of bearing an unsaturation or a $C_1-C_6$ alkyl radical bearing an aromatic or heterocyclic nucleus such as pyridine.

The compounds in accordance with the invention which are more particularly preferred are the compounds in which the alkyl group denotes, unless indicated otherwise, a group containing 2 to 12 carbon atoms and the aromatic nucleus preferably denotes phenyl.

The particularly preferred compounds defined above are those in which R is chosen from methyl, ethyl, butyl, isobutyl, n-hexyl, n-octyl, n-decyl, lauryl, 5-n-hexenyl, 2-ethylhexyl, 10-undecenyl, cyclohexyl, phenethyl or benzyl groups.

The particularly preferred compounds of the invention consist of 2,4-diamino-6-(n-butyloxy)pyrimidine 3-oxide, 2,4-diamino-6-ethyloxypyrimidine 3-oxide, 2,4-diamino-6-methoxypyrimidine 3-oxide, 2,4-diamino-6-n-hexyloxypyrimidine 3-oxide, 2,4-diamino-6-n-octyloxypyrimidine 3-oxide, 2,4-diamino-6-n-dodecyloxypyrimidine 3-oxide, 2,4-diamino-6-(2-ethylhexyloxy)-pyrimidine 3-oxide, 2,4-diamino-6-(5-n-hexenyloxy)-pyrimidine 3-oxide, 2,4-diamino-6-(10-undecenyloxy)-pyrimidine 3-oxide, 2,4-diamino-6-(2-phenylethyloxy)-pyrimidine 3-oxide, 2,4-diamino-6-(2-trifluoroethyloxy)pyrimidine 3-oxide, 2-amino-4-acetamido-6-butyloxypyrimidine 3-oxide, 2,4-di(benzyloxycarbonylamino)-6-butyloxypyrimidine 3-oxide, 2,4-di(methoxycarbonylamino)-6-butyloxypyrimidine3-oxide, 2,4-di(benzyloxycarbonylamino)-6-butyloxypyrimidine 3-oxide and N-(2-amino-6-butyloxy-4-pyrimidinyl)-N'-dimethyl-urea 3-oxide.

The compounds in accordance with the invention can also exist in their tautomeric form, corresponding to the following formulae (IA) and (IB):

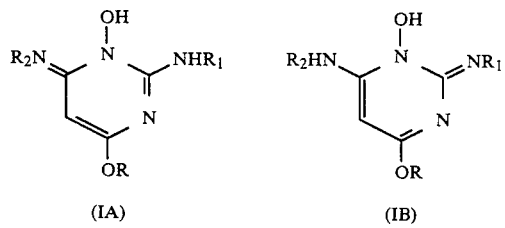

These tautomeric forms (I), (IA) and (IB) can be present in variable proportions and one can be predominant in relation to the others.

The compounds in accordance with the invention in which $R_1$ and $R_2$ denote hydrogen are prepared by starting with 2,4-diamino-6-(2,4-dichlorophenoxy)-pyrimidine 3-oxide or 2,4-diamino-6-chloropyrimidine 3-oxide, which is reacted with an alcoholate of formula $RO\ominus Y\oplus$ where R has the specification shown above and Y is an alkali metal cation such as sodium, potassium or lithium.

The compounds in which $R_1$ and $R_2$ are carbamoyl, alkoxycarbonyl or acyl groups are obtained from the corresponding 2,4-diamino-6-alkoxypyrimidine 3-oxide derivatives whose preparation is described hereinafter.

The formation of derivatives in which $R_1$ and $R_2$ are carbamoyl groups is generally obtained by reacting a carbamoyl chloride with the corresponding 2,4-diamino-6-alkoxypyrimidine 3-oxide derivative in a polar solvent such as dimethyl sulphoxide, at a temperature of between 0° and 100° C. and more particularly between 20° and 70° C.

The formation of derivatives in which $R_1$ and $R_2$ are alkoxycarbonyl groups is generally obtained by the action of an excess of a chloroformic ester on the corresponding 2,4-diamino-6-alkoxypyrimidine 3-oxide derivative, the operation being carried out in an aprotic polar solvent such as dichloromethane, in the presence of a tertiary amine such as triethylamine or pyridine, at a temperature of between 0° and 5020 C.

The formation of derivatives in which $R_1$ and $R_2$ are acyl groups is generally obtained by reacting an acid chloride or an anhydride with the corresponding 2,4-diamino-6-alkoxypyrimidine 3-oxide derivative in an aprotic polar solvent such as dichloromethane, in the presence of a tertiary amine such as triethylamine or pyridine, at a temperature of between 0° and 50° C.

Another subject of the invention consists in the use of certain derivatives of 2,4-diaminopyrimidine 3-oxide as intermediates for the preparation of oxadiazolopyrimidine derivatives by an elimination-cyclization reaction.

In fact, by starting with pyrimidine mono- or dicarbamate derivatives (where $R_1$ and $R_2$ have the meaning (C) defined above), or from mono- or diureidopyrimidine (where $R_1$ and $R_2$ have the meaning (B) defined above), it is possible to obtain oxadiazolopyrimidines according to the following reaction scheme:

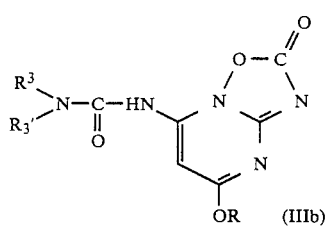

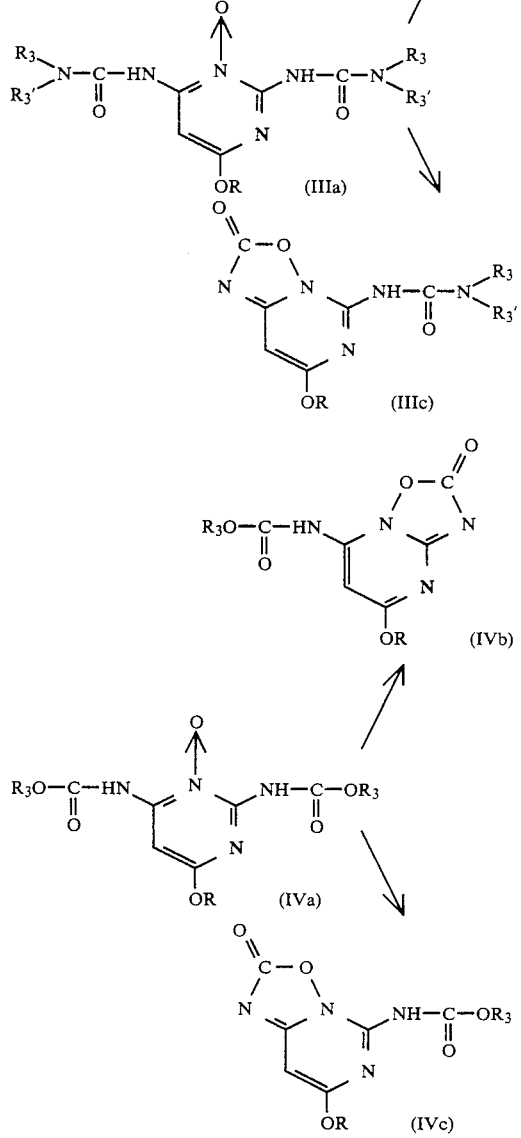

where R, $R_3$ and $R'_3$ have the meanings given above.

The diurea (IIa) is heated for a few hours to a temperature of between 50° and 120° C. in an organic solvent such as toluene, and leads to the oxadiazolopyrimidine of structure (IIIb).

By cyclizing, for example, a compound of formula (IVa) above, an oxadiazolopyrimidine of formula (IVb) is finally obtained. This known reaction is carried out by heating a compound of formula (IVa) to a temperature of approximately 50° to 200° C., preferably of approximately 100° to 150° C. The reaction can be carried out in the absence or in the presence of a solvent or of a mixture of solvents. If the reaction is carried out in a solvent or a mixture of solvents it will be possible to employ, in particular, aromatic hydrocarbons such as benzene, toluene or xylene, chlorinated hydrocarbons such as chloroform, alcohols such as butanol or isobutanol, ethers such as butyl ether, dioxane or diethylene glycol dimethyl ether, dimethylformamide, dimethyl sulphoxide and similar solvents or mixtures thereof.

The oxadiazolopyrimidines of formulae (IIIb) and (IVb) can be converted with the aid of inorganic or organic bases, in a manner which is known per se, into salts which are acceptable for pharmaceutical use.

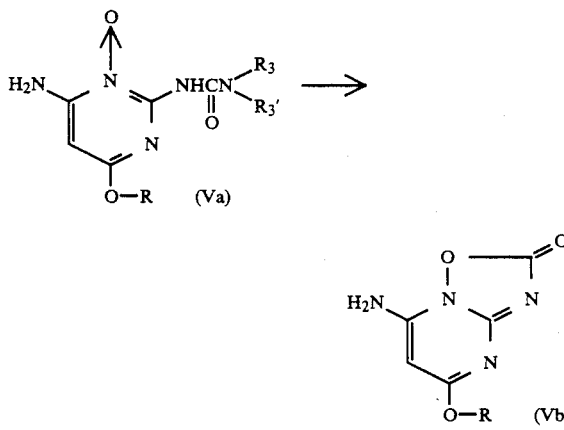

From the urea of formula (Va) the compound of formula (Vb), in accordance with the invention, is obtained quantitatively by heating the urea (Va) to a temperature of between 40° and 100° C. for a few hours in an organic solvent such as toluene.

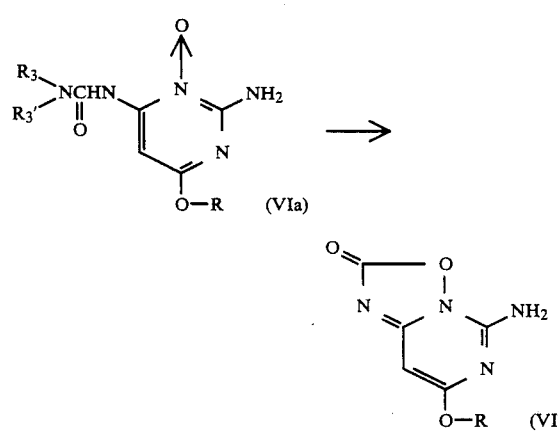

The isomeric form of structure (VIb), in accordance with the invention, is obtained by heating the urea of formula (VIa) in an organic solvent such as toluene or xylene to a temperature above 100° C. for a few hours.

Starting with the compounds of formula (I), it is possible to prepare their cosmetically or pharmaceutically acceptable acid addition salts, such as the salts of sulphuric, hydrochloric, hydrobromic, phosphoric, acetic, benzoic, salicylic, glycolic, succinic, nicotinic, tartaric, maleic, pamoic, methanesulphonic, picric, lactic and similar acids.

The compounds in accordance with the invention may be employed in the cosmetic or pharmaceutical field, especially in topical applications, and more particularly in the treatment or prevention of hair loss, and more particularly of pelada, of alopecia and of desquamative dermatitis.

These compositions are characterized essentially by the fact that they contain, in a physiologically acceptable medium suitable for a topical application, at least one compound corresponding to the formula (I) or one of its salts.

These compositions may comprise, as a physiologically acceptable medium, any medium which is appropriate for topical application either in cosmetics or in pharmacy and which is compatible with the active substance.

The compounds in accordance with the invention may be present in this medium either in the dissolved state or in the dispersed state, especially in micronized form.

The compositions intended to be employed in pharmacy are in the form of an ointment, tincture, cream, pomade, powder, patch, impregnated pad, solution, emulsion or vesicular emulsion, lotion, gel, spray or suspension. They may be either anhydrous or aqueous, depending on the clinical indication.

In these pharmaceutical compositions the compounds are present in concentrations of between 0.1 and 10% by weight, and in particular between 0.2 and 5% by weight.

The cosmetic compositions are especially intended to be employed in the form of a lotion, gel, soap, shampoo, aerosol or foam, and contain at least one compound of formula (I) or one of its salts, in a physiologically acceptable carrier.

The concentration of the compounds of formula (I) in these compositions is preferably between 0.01 and 7.5% by weight and in particular between 0.05 and 5% by weight.

The compositions in accordance with the invention may contain various additives usually employed in cosmetics or in pharmacy and in particular active substances such as hydrating agents like thiamorpholine and its derivatives or urea, antiseborrhoeic agents such as S-carboxymethylcysteine, S-benzylcysteamine and their derivatives, and thioxolone.

The compounds in accordance with the invention may be used in combination with compounds which further improve their activity relating to the fresh growth and/or the delaying of the loss of hair, such as more particularly the following compounds:

esters of nicotinic acid, including more particularly $C_1$-$C_6$ alkyl nicotinates and especially methyl nicotinate;

steroid and non-steroid antiinflammatory agents which are well known in the state of the art, and in particular hydrocortisone, its salts and its derivatives, niflumic acid, and the like;

retinoids and more particularly t-transretinoic acid, also known as tretinoin, isotretinoin, retinol or vitamin A and its derivatives, such as the acetate, palmitate or propionate, motretinide, etretinate and zinc t-transretinoate;

antibacterial agents chosen more particularly from macrolides, pyranosides and tetracyclines, and especially erythromycin;

calcium antagonist agents such as, more particularly, cinnarizine and diltiazem;

hormones such as estriol or analogues or thyroxine and its salts;

antiandrogen agents such as oxendolone, spironolactone and diethylstilbestrol; and scavengers of OH radicals, such as dimethyl sulphoxide.

It is also possible to use in combination with the compounds of the invention, optionally mixed with others, compounds such as the diazoxide corresponding to 3-methyl-7-chloro-2H-1,2,4-benzothiadiazine 1,1-dioxide, spiroxasone or 7-(acetylthio)-4',5'-dihydrospiro[androst-4-ene-17,2'-(3'H)furan]-3-one, phospholipids such as lecithin, linoleic and linolenic acids, salicyclic acid and its derivatives described in French Patent No. 2,581,542, and more particularly the salicylic acid derivatives bearing an alkanoyl group containing 2 to 12 carbon atoms in position 5 of the benzene ring, hydroxycarboxylic or ketocarboxylic acids and their esters, lactones and their corresponding salts, anthralin or 1,8,9-trihydroxyanthracene, carotenoids, eicosatetraynoic and eicosatriynoic acids and their esters and amides.

The compounds in accordance with the invention can also be used in combination with surface-active agents, more particularly including those chosen from nonionic and amphoteric surface-active agents.

Among the nonionic surfactants there will be mentioned especially the polyhydroxypropyl ethers described in French Patents Nos. 1,477,048, 2,091,516, 2,169,787, 2,328,763 and 2,574,786, oxyethylenated ($C_8$–$C_9$)alkylphenols containing from 1 to 100 moles of ethylene oxide and preferably 5 to 35 moles of ethylene oxide, and alkylpolyglycosides of formula:

$$C_nH_{2n+1}(C_6H_{10}O_5)_xH \quad (A)$$

in which n varies from 8 to 15 inclusive in x from 1 to 10 inclusive.

Among the amphoteric surface-active agents, more particular mention will be made of the amphocarboxyglycinates and the amphocarboxypropionates defined in the CTFA dictionary, 3rd edition, 1982, and sold, in particular, by Miranol under the name Miranol ®.

The compounds according to the invention may be introduced into carriers which further improve their activity with regard to fresh growth, while at the same time having properties which are advantageous from the cosmetic standpoint, such as volatile ternary mixtures of alkylene glycol or dialkylene glycol alkyl ether (alkyl and alkylene preferably being $C_1$ to $C_4$), ethyl alcohol and water, the glycolic solvent denoting more particularly ethylene glycol monoethyl ether, propylene glycol monomethyl ether or diethylene glycol monoethyl ether.

The compounds in accordance with the invention may also be introduced into gelled or thickened carriers such as essentially aqueous carriers gelled with heterobiopolysaccharides, such as xanthan gum or cellulose derivatives, hydroalcoholic carriers gelled with polyhydroxyethyl acrylate or methacrylate, or essentially aqueous carriers thickened, in particular, with polyacrylic acids crosslinked with a polyfunctional agent, such as the Carbopols sold by Goodrich.

These compositions may also contain preservatives, stabilizers, pH regulators, osmotic pressure modifiers, emulsifiers, UVA and UVB filters, and antioxidants such as α-tocopherol, butylhydroxyanisole or butylhydroxytoluene.

The physiologically acceptable medium may consist of water or a mixture of water and a solvent or a mixture of solvents, the solvents being chosen from organic solvents which are acceptable from a cosmetic or pharmaceutical standpoint and chosen more particularly from lower $C_1$–$C_4$ alcohols like ethyl alcohol, isopropyl lower alcohol, tert-butyl alcohol, alkylene glycols, alkylene glycol and dialkylene glycol alkyl ethers, such as ethylene glycol monoethyl ether, propylene glycol monomethyl ether or diethylene glycol monoethyl ether. When present, the solvents are present in proportions of between 1 and 80% by weight relative to the total weight of the composition.

The physiologically acceptable media may be thickened with the aid of thickening agents usually employed in cosmetics or pharmacy, and more particular mention may be made of heterobiopolysaccharides such as xanthan gum, scleroglucans, cellulose derivatives like cellulose ethers, and acrylic polymers, crosslinked or otherwise.

The thickeners are preferably present in proportions of between 0.1 and 5% by weight and in particular between 0.4 and 3% by weight relative to the total weight of the composition.

Another subject of the invention is a process for cosmetic treatment of hair or of the scalp, consisting in applying thereto at least one composition such as defined above, in order to improve the aesthetics of hair appearance.

A further subject of the invention consists in the use of the composition defined above for the preparation of a medication whose effect is to induce or to stimulate the growth of hair and to delay its loss.

The treatment consists chiefly in applying the composition such as defined above to the alopecic regions of the scalp of an individual.

The preferred method of application consists in applying 1 to 2 g of the composition to the alopecic region, at a frequency of one to two applications daily, for 1 to 7 days a week, this being done for a period of 1 to 6 months.

The compositions may be employed especially in the treatment of pelada, of hair loss or of desquamative dermatitis.

The following examples are intended to illustrate the invention without, however, being limiting in nature.

EXAMPLE 1

2,4-Diamino-6-(n-butyloxy)pyrimidine 3-oxide

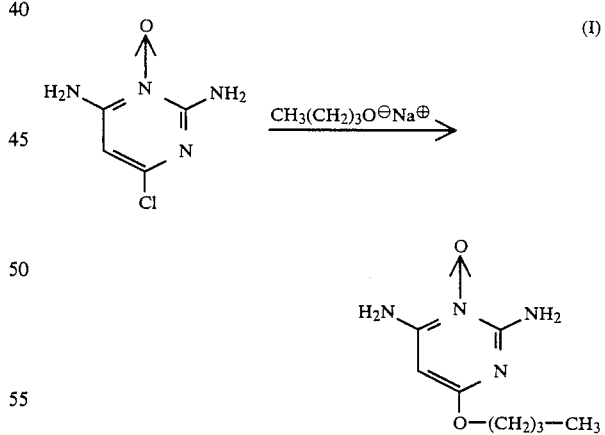

The compound (I) is obtained by reaction of sodium n-butylate with 2,4-diamino-6-chloropyrimidine 3-oxide.

Operating method 4 g of sodium are dissolved at 80° C. in 150 ml of dried n-butanol. After addition of 20 of 2,4-diamino-6-chloropyrimidine 3-oxide, the reaction mixture is refluxed for 24 hours.

After addition of 500 cm³ of dichloromethane, the insoluble material formed is filtered off. The organic phase is recovered, the solvent is evaporated off and the material is taken up in 500 cm³ of CH₂Cl₂, is washed with an aqueous solution saturated with NaCl, is dried over Na₂SO₄ and is evaporated to dryness.

The white precipitate obtained is taken up in CH₂Cl₂ and purified by precipitation from a methanol/hexane mixture 3.5 g of compound (I) are obtained.
Yield: 14%.
M.p.=166° C.

| Elemental analysis: $C_8H_{14}N_4O_2$; MW = 198. | | | | |
|---|---|---|---|---|
| | C | H | N | O |
| Calculated | 48.48 | 7.07 | 28.28 | 16.16 |
| Found | 47.87 | 7.11 | 27.97 | 16.24 |

The ¹H NMR and mass spectra are consistent with the expected structure.

Pharmacological results

In addition to its activity in preventing loss and stimulating fresh growth of hair, the compound (I) exhibits a weak antihypertensive effect on rats with spontaneous hypertension.

EXAMPLE 2

2,4-Diamino-6-ethyloxypyrimidine 3-oxide

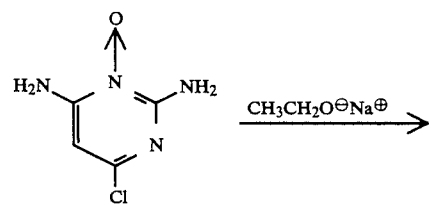

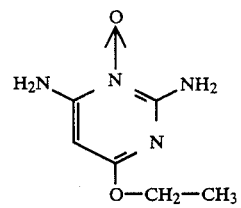

1.8 g of sodium are dissolved in 100 ml of ethanol. 10 g of 2,4-diamino-6-chloropyrimidine 3-oxide are added. The reaction mixture is refluxed until the starting material has disappeared and is heated to 120° C. in an autoclave for 7 hours. It is returned to ambient temperature and the insoluble material is filtered off and washed with ethanol.

The alcoholic phase is concentrated. Hydrochloric ethanol is added until the pH is acidic. After stirring, the hydrochloride is precipitated with anhydrous ether. It is filtered off and dried.

The white precipitate is taken up in H₂O (1 g in 10 cm³). The pH is made basic. After cooling, the precipitate is filtered off. It is washed with acetone and then with anhydrous ether.

| Elemental analysis: $C_6H_{10}N_4O_2$; MW = 170. | | | | |
|---|---|---|---|---|
| | C | H | 0 | N |
| Calculated | 42.35 | 5.88 | 18.52 | 32.94 |

| -continued | | | | |
|---|---|---|---|---|
| Elemental analysis: $C_6H_{10}N_4O_2$; MW = 170. | | | | |
| | C | H | 0 | N |
| Found | 42.41 | 6.04 | 19.03 | 32.69 |

The ¹H and ¹³C NMR and mass spectra are consistent with the expected structure.

Melting point: decomposition at about 252° C.

EXAMPLE 3

2,4-Diamino-6-methoxypyrimidine 3-oxide

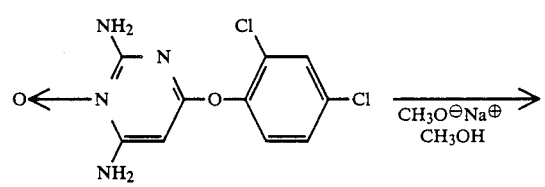

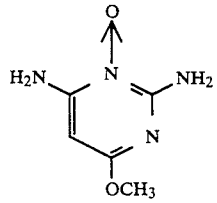

1.8 g of sodium are dissolved in 150 ml of methanol. 15 of 2,4-diamino-6-(2,4-dichlorophenoxy)pyrimidine 3-oxide are added and the reaction mixture is refluxed for 15 days.

The solvent is evaporated off and the residue obtained is chromatographed on silica gel (eluent: 85 ethyl acetate/15 methanol).

The white precipitate obtained is recrystallized from an acetonitrile/methanol mixture.

Yield=20%
M.p.=decomposition at 232° C.

| Elemental analysis: $C_5H_8N_4O_2$; MW = 156. | | | | |
|---|---|---|---|---|
| | C | H | N | O |
| Calculated | 38.46 | 5.13 | 35.90 | 20.51 |
| Found | 38.28 | 5.18 | 35.87 | 20.53 |

The ¹H NMR and mass spectra are consistent with the expected structure.

EXAMPLE 4

2,4-Diamino-6-n-hexyloxypyrimidine 3-oxide

The preparation is carried out following the operating procedure described in Example 3, with n-hexanol.
Temperature: 120° C., Time: 20 hours
Recrystallization from a methanol/ether mixture
Yield: 10%
M.p.=1842° C.

| Elemental analysis: $C_{10}H_{18}N_4O_2$; MW = 226. | | | | |
|---|---|---|---|---|
| | C | H | N | O |
| Calculated | 53.10 | 7.96 | 24.78 | 14.16 |
| Found | 52.99 | 7.96 | 24.75 | 14.34 |

The $^1$H NMR spectrum is consistent with the structure.

EXAMPLE 5

2,4-diamino-6-n-octyloxypyrimidine 3-oxide

The preparation is carried out following the operating method described in Example 3, using n-octanol.
Temperature: 110° C., Time: 17 hours
Recrystallization: methanol
Yield: 13.7%
M.p. = 138–139° C.

| Elemental analysis: $C_{12}H_{22}N_4O_2$; MW = 254. | | | |
|---|---|---|---|
| | C | H | N | O |
| Calculated | 56.69 | 8.66 | 22.05 | 12.60 |
| Found | 56.44 | 8.63 | 21.87 | 12.64 |

The $^1$H and $^{13}$C NMR and mass spectra are consistent with the structure.

EXAMPLE 6

2,4-Diamino-6-n-dodecyloxypyrimidine 3-oxide

The preparation is carried out following the operating method described in Example 3, using dodecanol.
Temperature: 110° C., Time: 20 hours
Yield: 25%
M.p. = 136° C.

| Elemental analysis: $C_{16}H_{30}N_4O_2$; MW = 310. | | | |
|---|---|---|---|
| | C | H | N | O |
| Calculated | 61.93 | 9.68 | 18.06 | 10.32 |
| Found | 62.01 | 9.76 | 17.96 | 10.45 |

The $^1$H and $^{13}$C NMR and mass spectra are consistent with the structure.

EXAMPLE 7

2,4-Diamino-6-(2-ethylhexyloxy)pyrimidine 3-oxide

The preparation is carried out following the operating method described in Example 3, using 2-ethylhexanol.
Temperature: 130° C., Time: 24 hours
Recrystallization: dichloromethane/methanol mixture
Yield: <10%
M.p. = 178°–180° C.

| Elemental analysis: $C_{12}H_{22}N_4O_2$; MW = 254. | | | |
|---|---|---|---|
| | C | H | N | O |
| Calculated | 56.69 | 8.66 | 22.05 | 12.60 |
| Found | 56.62 | 8.75 | 22.08 | 12.63 |

The $^{13}$C NMR and mass spectra are consistent with the structure.

EXAMPLE 8

2,4-Diamino-6-(5-n-hexenyloxy)pyrimidine 3-oxide

The preparation is carried out following the operating method described in Example 3, using 5-n-hexene-1-ol.
Temperature: 115° C., Time: 20 hours
Recrystallization: methanol
Yield: 37%
M.p. = 98–102° C.

| Elemental analysis: $C_{10}H_{16}N_4O_2$; MW = 224. | | | |
|---|---|---|---|
| | C | H | N | O |
| Calculated | 53.57 | 7.14 | 25.00 | 14.28 |
| Found | 53.68 | 7.15 | 25.04 | 14.40 |

The $^{13}$C NMR and mass spectra are consistent with the structure.

EXAMPLE 9

2,4-Diamino-6-(10-undecenyloxy)pyrimidine 3-oxide

The preparation is carried out following the operating method described in Example 3, using the alcohol 10-undecen-1-ol.
Temperature: 110° C., Time = 27 hours
Recrystallization: acetonitrile
Yield: 23%
M.p. = 131° C.

| Elemental analysis: $C_{15}H_{26}N_4O_2$; MW = 294. | | | |
|---|---|---|---|
| | C | H | N | O |
| Calculated | 61.22 | 8.84 | 19.05 | 10.88 |
| Found | 61.23 | 8.86 | 18.85 | 11.14 |

The $^1$H and $^{13}$C NMR and mass spectra are consistent with the structure.

EXAMPLE 10

2,4-Diamino-6-(2-phenylethyloxy)pyrimidine 3-oxide

The preparation is carried out following the operating method described in Example 1, using 2-phenylethyl alcohol.
Temperature: 115°–120° C., Time: 11 hours
Recrystallization: methanol
Yield: 18%
M.p. = 204° C.

| Elemental analysis: $C_{12}H_{14}N_4O_2$; MW = 246. | | | |
|---|---|---|---|
| | C | H | N | O |
| Calculated | 58.54 | 5.69 | 22.76 | 13.01 |
| Found | 58.51 | 5.69 | 22.58 | 13.16 |

The $^{13}$C NMR and mass spectra are consistent with the structure.

EXAMPLE 11

2-Amino-4-acetamido-6-butyloxypyrimidine 3-oxide

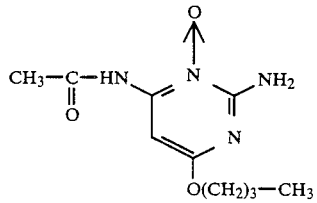

4.76 g of 2,4-diamino-6-n-butyloxypyrimidine 3-oxide and 300 ml of dichloromethane are introduced into a 500-ml three-necked round bottom flask fitted with a thermometer, a stirrer, a condenser and an argon inlet. They are heated until the solvent refluxes and a solution of 2.44 g of acetic anhydride in 30 ml of dichloromethane is added slowly.

After 10 minutes' introduction, the mixture is cooled to ambient temperature and transferred into a separating funnel.

The organic phase is washed until neutral and the solution is then concentrated under vacuum.

Hexane is added until a precipitate appears, which is filtered off. After dissolving in dichloromethane, it is precipitated a second time with hexane. The precipitate is recrystallized from an acetone/dichloromethane mixture and is then dried under vacuum.

2 g of a compound melting at 184° C. and consistent with the expected structure (mass and $^1$H NMR spectra) are obtained.

| Elemental analysis: $C_{10}H_{16}N_4O_3$; MW = 240. | | | | |
|---|---|---|---|---|
| | C | H | N | O |
| Calculated | 50.00 | 6.66 | 23.33 | 20.00 |
| Found | 50.04 | 6.72 | 23.34 | 20.11 |

EXAMPLE 12

2,4-Diacetamido-6-n-butyloxypyrimidine 3-oxide

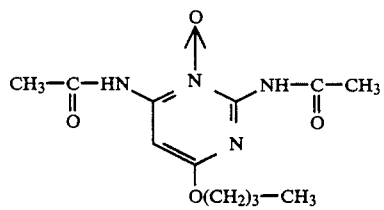

2 g of 2,4-diamino-6-n-butyloxypyrimidine 3-oxide, 20 ml of dichloromethane and 5.7 ml of triethylamine are introduced into a 50-ml three-necked round bottom flask fitted with a thermometer, a stirrer and an argon inlet.

They are cooled to −10° C. and 3.2 g of acetyl chloride are added over 30 minutes without exceeding 0° C.

10 ml of dichloromethane are added and the mixture is kept for another 2 hours 30 minutes at this temperature. It is transferred to a separating funnel and the organic phase is washed until neutral. After concentration under vacuum, hexane is added until a precipitate is obtained, which is filtered off. After recrystallization from an acetone/dichloromethane mixture, 1.5 g of a pure compound melting at 168° C. are obtained, whose mass and $^1$H NMR spectra confirm the expected structure.

| Elemental analysis: $C_{12}H_{18}N_4O_4$; MW = 282. | | | | |
|---|---|---|---|---|
| | C | H | N | O |
| Calculated | 51.06 | 6.38 | 19.86 | 22.69 |
| Found | 51.19 | 6.41 | 19.93 | 22.87 |

EXAMPLE 13

2,4-Di(methoxycarbonylamino)-6-butyloxypyrimidine 3-oxide 3 g of 2,4-diamino-6-n-butyloxypyrimidine 3-oxide, followed by 30 ml of dichloromethane and 12.8 ml of triethylamine, are introduced into a 100-ml three-necked round bottom flask fitted with a stirrer, a thermometer and an argon inlet.

The heterogeneous mixture is cooled to 0° C. and 8.5 g of methyl chloroformate are then run in over 1 hour 15 minutes without exceeding 0° C. The temperature is then allowed to rise to the ambient and stirring is continued for 23 hours more.

The mixture is then transferred into a separating funnel and the organic phase is washed with a 1% strength aqueous solution of hydrochloric acid and then with water until neutral.

The organic solvent is then evaporated off and the residue is taken up with ethyl ether and the white precipitate obtained is filtered off. It is taken up in 10 ml of refluxing methanol.

After cooling, filtration is carried out and, after drying, 3 g of a white compound are collected, melting at 142° C., the expected structure being confirmed by mass and $^{13}$C NMR spectra.

| Elemental analysis: $C_{12}H_{18}N_4O_6$; MW = 314. | | | | |
|---|---|---|---|---|
| | C | H | N | O |
| Calculated | 45.86 | 5.73 | 17.83 | 30.57 |
| Found | 45.72 | 5.77 | 17.62 | 30.86 |

EXAMPLE 14

2,4-Di(benzyloxycarbonylamino)-6-butyloxypyrimidine 3-oxide

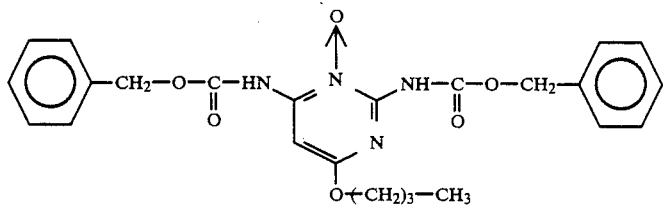

The procedure is the same as in Example 13, but with the introduction of 15.5 g of benzyl chloroformate in 1 hour 30 minutes at 0° C.

After 30 minutes the mixture is transferred to a separating funnel and the organic phase is washed with a 1% strength aqueous solution of hydrochloric acid and then with water until neutral. The solvent is then evaporated off under vacuum and the residue is then taken up with hexane until a white precipitate is obtained, which is filtered off. After redissolving in dichloromethane and precipitating with hexane, 4.1 g of a white compound, still containing traces of impurities, are obtained.

After recrystallization from an acetone/dichloromethane mixture, 3.6 g of a white product are obtained, melting at 146° C., its structure being confirmed by mass and $^{13}C$ NMR spectra.

| Elemental analysis: $C_{24}H_{26}N_4O_6$; M = 466. | | | | |
|---|---|---|---|---|
| | C | H | N | O |
| Calculated | 61.80 | 5.58 | 12.02 | 20.60 |
| Found | 61.78 | 5.56 | 11.88 | 20.73 |

EXAMPLE 15

N-(2-amino-6-butyloxy-4-pyrimidinyl),N,-dimethylurea 3-oxide

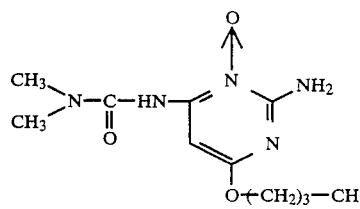

2 g of 2,4-diamino-6-n-butyloxypyrimidine 3-oxide, followed by 10 ml of dimethyl sulphoxide, are introduced into a 50 ml three-necked round bottom flask fitted with a condenser, a thermometer and an argon inlet.

The mixture is heated to 50° C. with stirring and 1.19 g of N-dimethylcarbamoyl chloride are then introduced over 5 minutes.

Stirring is continued for 2 hours 30 minutes more at 50° C. and the reaction mixture is then poured into 100 ml of water. It is then extracted with four 50 ml portions of dichloromethane. The combined organic fractions are evaporated to dryness and the residue taken up with ethyl ether.

An insoluble material is removed and the mother liquors are passed through a column of silica.

After elution with an ethyl acetate (90)/methanol (10) mixture, 1 g of a compound is recovered, melting at 122° C., whose mass and $^1H$ NMR spectra show that it corresponds to the expected structure.

| Elemental analysis: $C_{11}H_{19}N_5O_3$; MW = 269. | | | | |
|---|---|---|---|---|
| | C | H | N | O |
| Calculated | 49.07 | 7.06 | 26.02 | 17.84 |
| Found | 48.69 | 6.80 | 25.75 | 18.56 |

EXAMPLE OF COMPOSITION 1

The following composition is prepared:

| | |
|---|---|
| 2,4-Diamino-6-(n-butyloxy)pyrimidine 3-oxide | 3.0 g |
| Hydroxypropyl cellulose sold by Hercules under the trade name "Klucel G" | 3.0 g |
| Butylhydroxytoluene | 0.1 g |
| Ethanol/water mixture (50:50) q.s. | 100.0 g |

This composition is in the form of a gel.

1 to 2 g of this composition are applied to the alopecic regions of the scalp, optionally in combination with a massage to promote its entry, at a rate of one to two applications daily, for three months of treatment.

EXAMPLE OF COMPOSITION 2

The following composition is prepared:

| | |
|---|---|
| 2,4-Diamino-6-(n-butyloxy)pyrimidine 3-oxide | 6.0 g |
| Absolute ethanol/propylene glycol (95:5) mixture q.s. | 100.0 g |

EXAMPLE OF COMPOSITION 3

The following composition is prepared:

| | |
|---|---|
| 2,4-Diamino-6-(n-butyloxy)pyrimidine 3-oxide | 4.0 g |
| Propylene glycol | 20.0 g |
| Ethanol | 50.0 g |
| Water q.s. | 100.0 g |

EXAMPLE OF COMPOSITION 4

The following composition is prepared:

| | |
|---|---|
| 2,4-Diamino-6-(n-butyloxy)pyrimidine 3-oxide | 2.0 g |
| Methyl hydroxypropyl cellulose sold by Dow Chemical under the trade name "Methocel F" | 1.0 g |
| Ethanol | 36.0 g |
| Water q.s. | 100.0 g |

EXAMPLE OF COMPOSITION 5

The following composition is prepared:

| | |
|---|---|
| 2,4-Diamino-6-ethyloxypyrimidine 3-oxide | 2.5 g |
| Propylene glycol | 20.0 g |
| Ethanol | 40.0 g |
| Water q.s. | 100.0 g |

This composition is in the form of an active lotion against hair loss.

EXAMPLE OF COMPOSITION 6

A shampoo intended for the treatment of hair loss is prepared, of the following composition:

| | |
|---|---|
| 2,4-Diamino-6-n-butyloxypyrimidine 3-oxide | 2.0 g |
| Nonionic surfactant obtained by condensing 3.5 moles of glycidol with a $C_1$-$C_{14}$ α-diol according to French Patent No. 71-17206 | 13.0 g AS |
| Complexant (Fe Mascolate) | 0.2 g |
| Preservatives | 0.5 g |
| Water q.s. | 100.0 g |

EXAMPLE OF COMPOSITION 7

The following composition is prepared:

| | |
|---|---|
| 2,4-Diamino-6-n-butyloxypyrimidine 3-oxide | 0.3 g |
| Diglycerol hexadecyl ether of formula $C_{16}H_{33}$—O($CH_2$—CHOH—$CH_2$—O$)_2$H | 3.8 g |
| Cholesterol | 3.8 g |
| Acylglutamate HS11 sold by Ajinomoto | 0.4 g |
| Preservatives | 0.4 g |
| Water q.s. | 100.0 g |

This composition is in the form of a vesicular emulsion.

EXAMPLE OF COMPOSITION 8

A lotion of the following composition is prepared:

| | |
|---|---|
| 2,4-Diamino-6-(2-phenylethyloxy)pyrimidine 3-oxide | 5.0 g |
| Propylene glycol | 22.8 g |
| Ethanol | 55.1 g |
| Water q.s. | 100.0 g |

EXAMPLE OF COMPOSITION 6

A lotion of the following composition is prepared:

| | |
|---|---|
| 2,4-Diamino-6-(2-phenylethyloxy)pyrimidine 3-oxide | 4.0 g |
| Propylene glycol | 6.45 g |
| Absolute ethanol q.s. | 100.0 g |

EXAMPLE OF COMPOSITION 10

A lotion of the following composition is prepared:

| | |
|---|---|
| 2,4-Diamino-6-(2-phenylethyloxy)pyrimidine 3-oxide | 2.5 g |
| Ethanol | 50.0 g |
| Water q.s. | 100.0 g |

1 to 2 ml of these lotions are applied to the alopecic regions of the scalp; these applications, optionally in combination with a massage to promote entry, being performed once or twice daily.

We claim:

1. Compound characterized in that it corresponds to the formula:

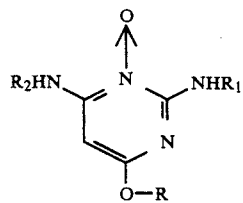

in which:

$R_1$ and $R_2$ denote, independently of each other, a hydrogen atom, a carbamoyl group of formula:

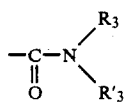

with $R'_3 = H$ or $R_3$;
an alkoxycarbonyl group of formula:

or an acyl group of formula:

in which formulae $R_3$ denotes a linear or branched $C_1$-$C_{18}$ alkyl radical, a $C_2$-$C_{18}$ alkenyl group or a $C_5$-$C_8$ cycloalkyl group; $R_3$ may also denote an aryl or aralkyl radical corresponding to the formula:

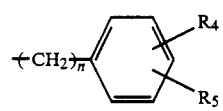

in which:

n is between 0 and 4l;

$R_4$ and/or $R_5$, independently of each other, denote hydrogen, a lower $C_1$-$C_6$ alkyl group, a hydroxyl or alkoxy group or a halogen atom, at least one of the radicals $R_1$ or $R_2$ being different from hydrogen;

R denotes a linear or branched $C_1$-$C_{18}$ alkyl or $C_2$-$C_{18}$ alkenyl radical, a $C_4$-$C_6$ cycloalkyl radical capable of bearing an unsaturation or a $C_1$-$C_6$ alkyl radical bearing a phenyl group or a pyridine ring.

2. Compound according to claim 1, characterized in that the radical R is chosen from methyl, ethyl, butyl, isobutyl, n-hexyl, n-octyl, n-decyl, lauryl, 2-ethylhexyl, 5-n-hexenyl, 10-undecenyl, cyclohexyl, phenethyl or benzyl groups.

3. Compound according to claim 1, characterized in that it is 2,4-diamino-6-(n-butyloxy)pyrimidine 3-oxide and its cosmetically or pharmaceutically acceptable salts.

4. Compound according to claim 1, characterized in that it is 2,4-diamino-6-ethyloxypyrimidine 3-oxide or its cosmetically or pharmaceutically acceptable salts.

5. Compound according to claim 1, characterized in that it is chosen from 2-amino-4-acetamido-6-butyloxypyrimidine 3-oxide, 2,4-diacetamido-6-butyloxypyrimidine3-oxide, 2,4-di(methoxycarbonylamino)-6-butyloxypyrimidine3-oxide, 2,4-di(benzyloxycarbonylamino)-6-butyloxypyrimidine 3-oxide and N-(2-amino-6-butyloxy-4-pyrimidinyl)-N'-dimethylurea 3-oxide and its cosmetically or pharmaceutically acceptable salts.

6. Compound of the group of 2,4-diaminopyrimidine 3-oxides, chosen from 2,4-diamino-6-methoxypyrimidine 3-oxide, 2,4-diamino-6-n-hexyloxypyrimidine 3-oxide, 2,4-diamino-6-n-octyloxypyrimidine 3-oxide, 2,4-diamino-6-n-dodecyloxypyrimidine 3-oxide, 2,4-diamino-6-(2-ethylhexyloxy)pyrimidine 3-oxide, 2,4-diamino-6-(5-n-hexenyloxy)pyrimidine 3-oxide, 2,4-diamino-6-(10-undecenyloxy)pyrimidine 3-oxide, 2,4-diamino-6-(2-phenylethyloxy)pyrimidine 3-oxide, or cosmetically or pharmaceutically acceptable salts.

7. Composition intended to be employed in topical application, characterized in that it contains, in a physiologically acceptable medium, at least one compound as defined in claim 1, in an effective amount for topical application.

8. The compositions intended to be employed in therapeutic treatment of hair loss according to claim 7, characterized in that it is in the form of an ointment tincture, cream, pomade, powder, patch, impregnated pad, solution, emulsion, vesicular emulsion, lotion, gel, spray or anhydrous or aqueous, suspension, and that it contains in a pharmaceutically acceptable medium, at least one compound as defined in claim 1, in concentrations of between 0.1 and 10% by weight relative to the total weight of the composition.

9. Composition intended to be employed in cosmetics, such as defined in claim 7, characterized in that it is in the form of a lotion, gel, soap, shampoo, aerosol or foam and that it contains, in a cosmetically acceptable carrier, at least one compound such as defined in claim 1, in a concentration of between 0.01 and 7.5% by weight.

10. Composition according to claim 7, characterized in that, in addition to hydrating agents, it contains antiseborrhoeic agents.

11. Composition according to claim 7, characterized in that it also contains agents which further improve the activity of the compounds of formula (I) relating to the fresh growth and delaying the loss of hair, the said agents are selected from the group consisting of nicotinic acid esters, steroid or nonsteroid antiinflammatory agents, retinoids, antibacterial agents, calcium antagonist agents, hormones, antiandrogen agents or scavengers for OH radicals, diazoxide, spiroxazone, phospholipids, linolenic and linoleic acids, salicylic acid and its derivative, hydroxycarboxylic or ketocarboxylic acids, their esters, lactones and their corresponding salts, anthralin or 1,8,9-trihydroxyanthracene, carotenoids, 5,8,11,14-eicosatetraynoic and 5,8,11-eicosatriynoic acids and their esters and amides, and mixtures thereof.

12. Composition according to claim 7, characterized in that the physiologically acceptable medium consists of water, a mixture of water and of one or more organic solvent(s) or of a mixture of organic solvents, the organic solvents being pharmaceutically or cosmetically acceptable.

13. Composition according to claim 12, characterized in that the solvents are chosen from lower $C_1$–$C_4$ alcohols, alkylene glycols and mono- and dialkylene glycol alkyl ethers.

14. Composition according to claim 7, characterized in that the physiologically acceptable medium is thickened by means of thickening or gelling agents and contains preservatives, stabilizers, pH regulators, osmotic pressure modifiers, emulsifiers, UVA and UVB filters and antioxidants.

15. Composition according to claim 14, characterized in that it also contains surface-active agents chosen from nonionic and amphoteric surface-active agents.

16. Process for cosmetic treatment of hair or of the scalp, characterized in that the composition such as defined in claim 9 is applied.

17. Method of use of a composition according to claim 7 in the therapeutic treatment of hair loss comprising applying an effective amount of said composition to the hair or the scalp.

18. Composition according to claim 8 in which the concentration of the compound of claim 1 is between 0.2 and 5% by weight relative to the total weight of the composition.

* * * * *